US010402537B2

(12) United States Patent
Segawa et al.

(10) Patent No.: US 10,402,537 B2
(45) Date of Patent: Sep. 3, 2019

(54) REMOTE INTERPRETATION SYSTEM AND METHOD FOR MANAGEMENT OF INTERPRETATION REQUEST INFORMATION AND INTERPRETATION RESULT INFORMATION

(71) Applicant: CANON KABUSHIKI KAISHA, Tokyo (JP)

(72) Inventors: Akimichi Segawa, Ichikawa (JP); Kazuki Takahashi, Yokohama (JP); Masayuki Hayashi, Funabashi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/222,766

(22) Filed: Jul. 28, 2016

(65) Prior Publication Data
US 2017/0032549 A1 Feb. 2, 2017

(30) Foreign Application Priority Data

Jul. 31, 2015 (JP) ................. 2015-152066

(51) Int. Cl.
G06F 19/00 (2018.01)
G16H 10/60 (2018.01)
(52) U.S. Cl.
CPC ........... G06F 19/321 (2013.01); G16H 10/60 (2018.01)
(58) Field of Classification Search
CPC .............................. G06T 11/206; G06F 19/321
USPC ....................................................... 345/440
See application file for complete search history.

(56) References Cited

U.S. PATENT DOCUMENTS

| 2007/0016442 | A1* | 1/2007 | Stroup | G06Q 50/22 705/2 |
| 2008/0294663 | A1* | 11/2008 | Heinley | G06F 3/0481 |
| 2009/0192823 | A1* | 7/2009 | Hawkins | G06F 19/321 705/3 |
| 2009/0222286 | A1* | 9/2009 | Elsholz | G06F 19/322 705/3 |
| 2012/0131507 | A1* | 5/2012 | Sparandara | G16H 10/60 715/833 |
| 2016/0350480 | A1* | 12/2016 | Gerdeman | G06F 19/321 |
| 2017/0116382 | A1* | 4/2017 | Reminick | G16H 10/65 |

FOREIGN PATENT DOCUMENTS

| JP | H10257188 A | 9/1998 |
| JP | 2009-518732 A | 5/2009 |
| JP | 2012079200 A | 4/2012 |
| JP | 2013025388 A | 2/2013 |

(Continued)

Primary Examiner — Shivang I Patel
(74) Attorney, Agent, or Firm — Canon U.S.A. Inc., IP Division

(57) ABSTRACT

Display control is performed for generation of a timeline screen in such a way that requester-side event information corresponding to request information is to be displayed at one of display areas separated from each other by a timeline axis on the timeline screen and that interpreter-side event information corresponding to radiological interpretation result information is to be displayed at the other of the display areas on the timeline screen, wherein the timeline axis is generated on the basis of time-and-date information of the request information and of the radiological interpretation result information determined on the basis of patient information.

14 Claims, 22 Drawing Sheets

(56) References Cited

FOREIGN PATENT DOCUMENTS

| | | | |
|---|---|---|---|
| JP | 2013242745 | A | 12/2013 |
| JP | 2014153920 | A | 8/2014 |
| JP | 2014532217 | A | 12/2014 |
| JP | 2015138518 | A | 7/2015 |
| JP | 2015521308 | A | 7/2015 |
| WO | 2011122404 | A1 | 10/2011 |

\* cited by examiner

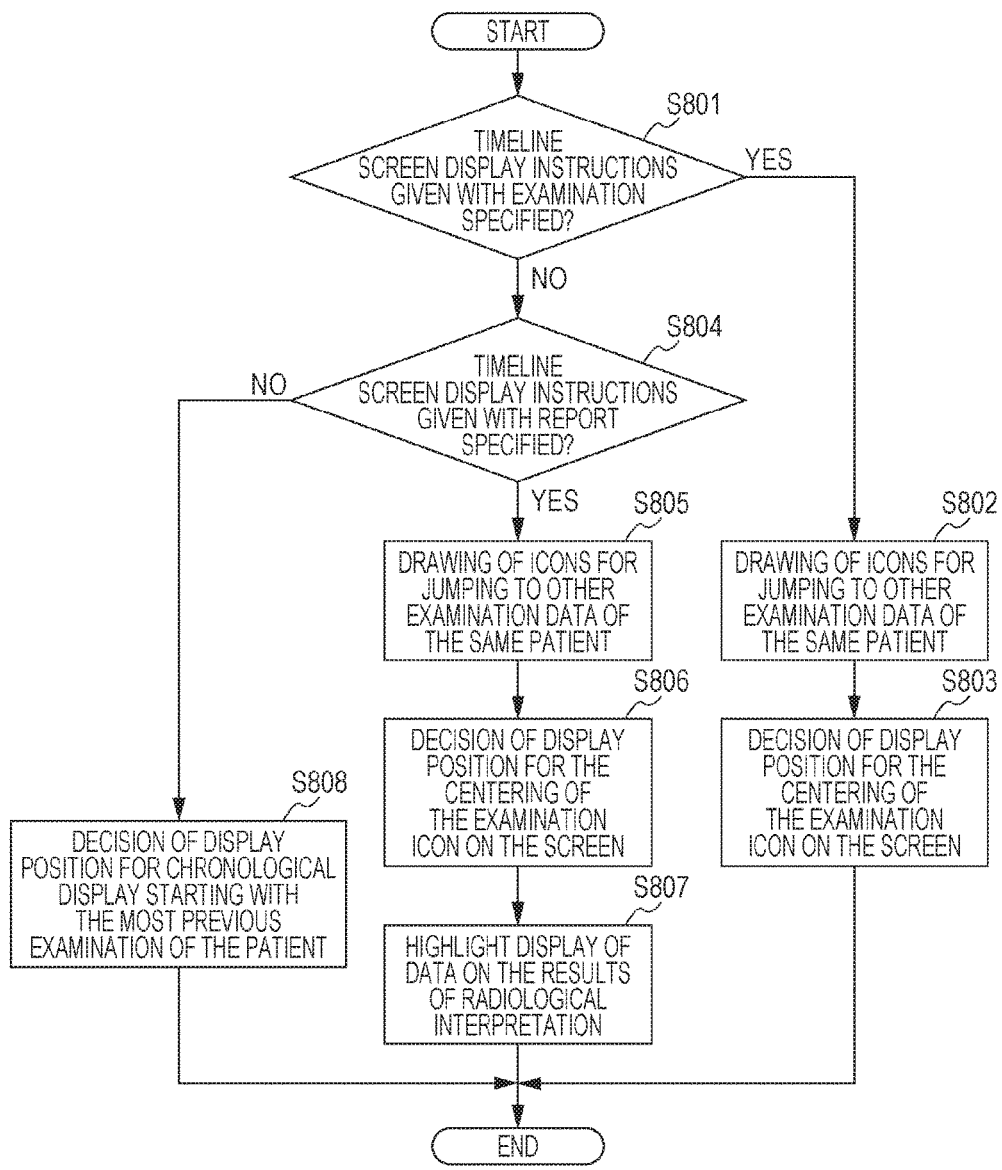

FIG. 9A

| USER ID (901) | USER NAME (902) | ROLE (903) |
|---|---|---|
| 1 | DOKUEI TAROE | DIAGNOSTICIAN |
| 2 | DOKUEI JIRO | DIAGNOSTICIAN |
| 3 | DOKUEI SABURO | DIAGNOSTICIAN |
| 4 | JIMUIN A | CLERK |
| 5 | IRAI TARO | CLERK |
| 6 | DOKUEI SHIRO | DIAGNOSTICIAN |
| 7 | IRAI JIRO | CLERK |

FIG. 9B

| REQUESTING FACILITY ID (911) | REQUESTING FACILITY NAME (912) |
|---|---|
| 1 | KANNON HOSPITAL |
| 2 | HOSPITAL A |
| 3 | HOSPITAL B |

FIG. 9C

| REQUESTING FACILITY ID (921) | PATIENT ID (922) | PATIENT NAME (923) | BIRTH DATE (924) |
|---|---|---|---|
| 1 | 101 | KANNON TARO | 1/19/1979 |
| 1 | 102 | KIYA OTOTA | 1/19/1955 |
| 2 | 401 | KANJYA A | 8/18/1971 |
| 2 | 402 | KANJYA B | 5/12/1968 |
| 2 | 405 | KANJYA C | 7/3/1949 |

FIG. 9D

| REQUEST ID | REQUESTING FACILITY ID | PATIENT ID | REQUEST DATE | EXAMINATION ID | EXAMINATION TYPE | EXAMINED REGION OF BODY | REQUEST STATUS | REQUEST RECEPTIONIST USER |
|---|---|---|---|---|---|---|---|---|
| 1001.2001.3221 | 1 | 101 | 2/24/2014 | 1024.2048.4096 | MR | ENTIRE REGION OF THROAT AND NECK | INTERPRETATION DONE | IRAI TARO |
| 1001.3045.224 | 1 | 102 | 1/25/2015 | 1024.6561.2430 | MR | ENTIRE REGION OF THROAT AND NECK | INTERPRETATION DONE | IRAI JIRO |
| 1001.3057.228 | 1 | 102 | 2/24/2013 | 1024.2187.6561 | MR | THROAT | INTERPRETATION DONE | IRAI TARO |
| 1001.3068.445 | 2 | 405 | 3/1/2014 | 2187.6561.2430 | CT | ABDOMEN | INTERPRETATION DONE | JIMUIN A |
| 1001.3067.300 | 2 | 401 | 2/2/2015 | 1587.6645.8512 | CT | THROAT | NOW UNDER INTERPRETATION | IRAI TARO |

| EXAMINATION UID 1001 | EXAMINATION DATE 1002 | MODALITY TYPE 1003 | REQUESTING FACILITY ID 1004 | PATIENT ID 1005 | IMAGE ID 1006 |
|---|---|---|---|---|---|
| 1024.2048.4096 | 2/24/2014 12:15 | MR | 1 | 101 | A01.0001 |
| 2187.6561.2430 | 2/25/2014 17:30 | MR | 2 | 401 | A11.0002, A11.0004 |
| 2187.6561.2430 | 2/25/2014 17:30 | MR | 2 | 401 | A11.0002, A11.0004 |
| 1024.6561.2430 | 1/24/2015 12:15 | CT | 1 | 102 | A01.0006 |
| 1024.2187.6561 | 2/11/2013 10:40 | CT | 1 | 102 | A01.0008 |
| 1001.3067.300 | 1/15/2014 | CT | 2 | 401 | A01.0009 |

FIG. 10B

| REPORT ID 1011 | REQUESTING FACILITY ID 1012 | REQUEST ID 1013 | PATIENT ID 1014 | STATUS 1015 | DIAGNOSTICIAN IN CHARGE 1016 | RADIOLOGICAL INTERPRETATION DATE 1017 | TARGET REGION OF BODY 1018 | RADIOLOGICAL INTERPRETATION RESULT 1019 |
|---|---|---|---|---|---|---|---|---|
| 11 | 1 | 1001.2001.3221 | 101 | CONFIRMED | DOKUEI SABURO | 2/25/2014 | NECK | SUSPECTED OF CERVICAL SPONDYLOSIS |
| 12 | 1 | 1001.3045.224 | 102 | CONFIRMED | DOKUEI SIRO | 1/26/2015 | THROAT, NECK | SUSPECTED OF CERVICAL SPONDYLOSIS |
| 13 | 1 | 1001.3067.228 | 102 | CONFIRMED | DOKUEI SABURO | 2/25/2013 | THROAT | SUSPECTED OF MALIGNANT TUMOR |
| 14 | 2 | 1001.3067.300 | 401 | NOT YET | DOKUEI TARO | | THROAT | |

FIG. 10C

| THREAD ID 1021 | THREAD TITLE 1022 | THREAD OWNER 1023 | PARTICIPANTS 1024 | REQUESTING FACILITY ID 1025 | PATIENT ID 1026 |
|---|---|---|---|---|---|
| 1 | RE: MR REPORT | DOKUEI SABURO | DOKUEI SABURO, IRAI TARO | 1 | 101 |
| 2 | EXAMINATION INFORMATION | JIMUIN A | DOKUEI JIRO, DOKUEI SABURO | 2 | 401 |
| 3 | RELEVANT REPORT INFORMATION | DOKUEI TARO | DOKUEI TARO, JIMUIN A | 2 | 402 |

FIG. 10D

| MESSAGE ID | THREAD ID | USER NAME | TRANSMISSION DATE | MESSAGE TEXT |
|---|---|---|---|---|
| 1001 | 1 | DOKUEI SABURO | 5/1/2014 16:30 | Regarding the MR report dated Feb. 25, please tell us the name of the disease if confirmed. |
| 1002 | 1 | IRAI TARO | 5/1/2014 18:30 | As a result of ..., a diagnosis of ... has been confirmed. For more information, please contact ... at Kannon Hospital. |
| 1003 | 2 | JIMUIN A | 6/1/2014 17:00 | No change is necessary for ... |
| 1004 | 2 | DOKUEI TARO | 6/1/2014 18:00 | Got it. |
| 1005 | 3 | DOKUEI TARO | 6/7/2014 15:30 | There is no relevant report. |

FIG. 12

| Status | Request | Image | Remarks | Timeline | Requester | Patient ID | Patient name | Age | Gender | Exam. type | Region examined | Request date |
|---|---|---|---|---|---|---|---|---|---|---|---|---|
| Interpretation done | | | | | Kannon Hospital | 101 | Kannon Taro | 36 | Male | MR | ENTIRE REGION OF THROAT AND NECK | 2/24/2014 |
| Interpretation done | | | | | Kannon Hospital | 102 | Kiya Otota | 60 | Male | MR | ENTIRE REGION OF THROAT AND NECK | 1/25/2015 |
| Interpretation done | | | | | Kannon Hospital | 102 | Kiya Otota | 60 | Male | MR | THROAT | 2/24/2013 |
| Interpretation done | | | | | Hospital A | 405 | Kanjya C | 66 | Female | CT | ABDOMEN | 3/1/2014 |

FIG. 13

Work List ~1301

| Status | Requesting facility ID | Patient ID | Request date | Exam. date |
|---|---|---|---|---|
| Now under interpretation | Hospital A | Patient A | 2/2/2015 | 1/15/2014 |

1311  1312  1313  1314  1315

🔍 Search ~1321
Requester [Kannon Hospital ▽] ~1322
Patient ID [         ] ~1323
Patient name [         ] ~1324

[Clear]  [Search] ~1325

Search ~1331

| Requesting facility ID | Patient ID | Request date | Region examined | Status | Region examined |
|---|---|---|---|---|---|
| Kannon Hospital | Kannon Taro | 2/24/2014 | ENTIRE REGION OF THROAT AND NECK | Confirmed | ENTIRE REGION OF THROAT AND NECK |
| Kannon Hospital | Kiya Obota | 1/25/2015 | ENTIRE REGION OF THROAT AND NECK | Confirmed | ENTIRE REGION OF THROAT AND NECK |
| Kannon Hospital | Kiya Obota | 2/24/2013 | THROAT | Confirmed | THROAT |

1332  1333  1334  1335  1336  1337

1338

[Enter remarks] [Display images] [Timeline] [Return]
1341          1342            1343      1344

FIG. 14A

| TIME AND DATE OF EVENT OCCURRENCE (1401) | PLACE OF OCCURRENCE (1402) | EVENT CLASS (1403) | DISPLAY DATA (1404) |
|---|---|---|---|
| 2/24/2014 12:15 | KANNON HOSPITAL | EXAMINATION CONDUCTED | exam = "MR Neck Standard" image = 0001011.jpg |
| 2/24/2014 16:30 | KANNON HOSPITAL | REQUEST RECEIVED | user = "Irai Taro" orderDetail = "MR entire region of throat and neck" part = "entire region of throat and neck" |
| 2/25/2014 10:30 | RADIOLOGICAL INTERPRETATION CENTER | RESULTS OF RADIOLOGICAL INTERPRETATION | user = "Dokuei Saburo" detail = "suspected of cervical spondylosis" part = "neck" |
| 5/1/2014 16:30 | RADIOLOGICAL INTERPRETATION CENTER | MESSAGE | user = "Dokuei Saburo" threadTitle = "Re: MR report" messageID = 10001 messageTitle = "Regarding the MR report dated Feb. 25, please... the name of the disease if confirmed." |
| 5/1/2014 18:30 | KANNON HOSPITAL | MESSAGE | user = "Irai Taro" threadTitle = "Re: MR report" messageID = 10002 messageTitle = "As a result of ..., a diagnosis of ... has been confirmed. ..." |

FIG. 14B

| TIMELINE DISPLAY YEAR/MONTH (1411) | THE NUMBER OF EVENTS OCCURRED (1412) |
|---|---|
| FEBRUARY 2014 | 3 |
| MARCH 2014 | 0 |
| APRIL 2014 | 0 |
| MAY 2014 | 2 |

REMOTE INTERPRETATION SYSTEM AND METHOD FOR MANAGEMENT OF INTERPRETATION REQUEST INFORMATION AND INTERPRETATION RESULT INFORMATION

BACKGROUND

Field

The disclosed technique relates to an information processing system, an information processing apparatus, and a server apparatus.

Description of the Related Art

In medical practice, a patient undergoes radiological examination and interpretation more than once so that the health status of the patient can be monitored over time for follow-up assessment. "Modality" such as CT, MRI, US, or PET is used for radiological examination. The examination history of a patient will be easier to view if displayed in time series on a display screen. For this reason, the history of medical events is displayed on a timeline.

A system for displaying all events pertaining to a particular patient on the patient's timeline is disclosed in PCT Japanese Translation Patent Publication No. 2009-518732.

A diagnostician who reads an image that was captured using modality to make a diagnosis based on radiological interpretation is not stationed on duty at every hospital. Therefore, these days, it is nothing unusual to request a diagnostician working at other hospital or at a remote place to conduct a radiological interpretation remotely.

There is a need for an improved communication system (remote radiological interpretation system) for remote interaction between a requesting facility, which is a requester of such radiological interpretation, and a diagnostician who is asked to conduct a radiological interpretation (radiological interpretation facility).

Timeline display for visualization of the medical history of a patient is demanded in such a remote radiological interpretation system, too. However, if the method disclosed in PCT Japanese Translation Patent Publication No. 2009-518732 is applied to it, there is a concern that the user might find it visually confusing because radiological interpretation request information and a radiological interpretation result, that is, the outcome of a diagnosis, are displayed in a mixed manner.

SUMMARY

In management of requests for radiological interpretation of medical images and the results of radiological interpretation conducted on the basis of the requests, the disclosed technique provides, in one of its aspects, a system for generating an easy-to-view timeline screen for visualization of the medical history of a patient.

An information processing system according to the disclosed technique is a system for management of request information sent together with a medical image from a requesting facility and management of radiological interpretation result information, which is information on results of radiological interpretation conducted at a radiological interpretation facility by using the medical image sent together with the request information from the requesting facility, comprising: a storage unit configured to store the request information and the radiological interpretation result information in association with patient information; a receiving unit configured to receive a request for timeline screen display, with the patient information specified; a determination unit configured to determine the request information and the radiological interpretation result information associated with the patient information specified for the request received by the receiving unit; and a display control unit configured to perform control for generation of a timeline screen in such a way that requester-side event information corresponding to the request information is to be displayed at one of display areas separated from each other by a timeline axis on the timeline screen and that interpreter-side event information corresponding to the radiological interpretation result information is to be displayed at the other of the display areas on the timeline screen, the timeline axis being generated on the basis of time-and-date information of the request information and of the radiological interpretation result information determined by the determination unit.

Further features of the present invention will become apparent from the following description of exemplary embodiments with reference to the attached drawings.

BRIEF DESCRIPTION OF THE DRAWINGS

FIG. 8 is a flowchart for explaining the procedure of screen display position decision processing.

FIG. 9A is a diagram that illustrates an example of one of data tables managed in a database.

FIG. 9B is a diagram that illustrates an example of another one of the data tables managed in the database.

FIG. 9C is a diagram that illustrates an example of another one of the data tables managed in the database.

FIG. 9D is a diagram that illustrates an example of another one of the data tables managed in the database.

FIG. 10A is a diagram that illustrates an example of another one of the data tables managed in the database.

FIG. 10B is a diagram that illustrates an example of another one of the data tables managed in the database.

FIG. 10C is a diagram that illustrates an example of another one of the data tables managed in the database.

FIG. 10D is a diagram that illustrates an example of another one of the data tables managed in the database.

FIG. 12 is a diagram that illustrates an example of a screen on which radiological interpretation list selection can be made.

FIG. 13 is a diagram that illustrates an example of a screen on which report selection can be made.

FIG. 14A is a diagram that illustrates an example of an event table.

FIG. 14B is a diagram that illustrates an example of a timeline table.

DESCRIPTION OF THE EMBODIMENTS

With reference to the accompanying drawings, an exemplary embodiment of the present invention will now be explained. The configuration described below is a mere example. The scope of the present invention shall not be construed to be limited to the exemplary configuration.

System Configuration

Figure 1:
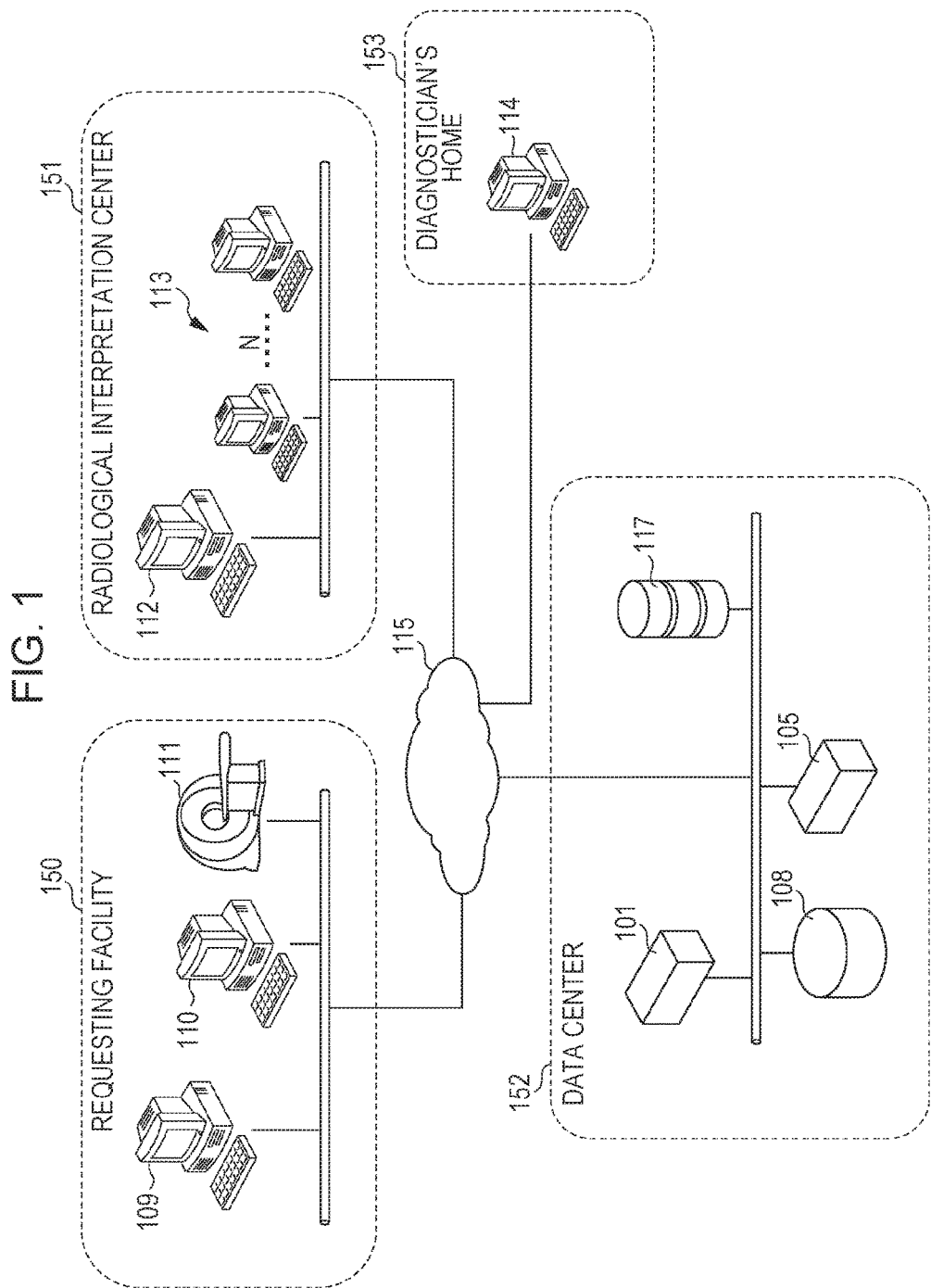
FIG. 1 is a diagram that illustrates an example of system configuration according to an exemplary embodiment.

FIG. 1 is a view of the overall configuration of a remote radiological interpretation system shown as an example of an information processing system according to an exemplary embodiment. In the present embodiment, the remote radiological interpretation system includes, as its stations, a data center, requesting facilities, a radiological interpretation center, and diagnostician's home. These stations are connected to one another via a communication network 115. In the present embodiment, the requesting facility is defined as "the requester side", and the radiological interpretation center and the diagnostician are defined as "the interpreter side".

Each user of the remote radiological interpretation system is required to go through an authentication process when starting an access from an information processing apparatus (109, 112, 113, 114), specifically, from a client terminal installed in the corresponding station. An authentication function provided by an authentication server (not illustrated), which is installed in the data center, is used for authentication. After successful authentication, a portal page appears on the display screen of the information processing apparatus of the authenticated user. Authentication information may have been transmitted to the data center for registration in advance.

At a requesting facility 150, modality 111, which is an image capturing machine such as CT, MRI, US, or PET, acquires image data (medical image data) of a patient for remote radiological interpretation use. After the image capturing, the image data is transmitted to an image relaying client 110 inside the requesting facility 150. The image data is, for example, data conforming to the DICOM (Digital Imaging and Communication in Medicine) standard. The image relaying client 110 archives the image data transmitted from the modality 111, and, after that, transmits the image data to an image management server 101 installed in a data center 152. The image management server 101 issues and assigns a unique ID (identification information) to each piece of image data. The ID-assigned data is stored into an external storage device 117. The image data conforming to the DICOM standard is made up of image data content, patient information such as the name, ID, and gender of a patient, and accompanying information including imaging conditions such as modality type. As described above, the image data acquired by the modality 111 at the requesting facility is transmitted to the data center and is then registered into the external storage device 117.

Using a requesting terminal 109, a person in charge of requesting for radiological interpretation at the requesting facility 150 enters information needed when s/he makes a request for radiological interpretation (request information). The request information is transmitted together with the image data to the data center 152. Each piece of request information is stored into a database 108. In the database 108, the request information is managed with a link to the requesting facility information and to the patient information in an associated manner. In this specification, the request information and the image data correspond to each other. The distribution (assignment) of the request information is treated as the distribution of the image data.

Using a work terminal 112, a person in charge of receiving requests from the requesting facility 150 for radiological interpretation at a radiological interpretation center 151 checks whether there is any information missing in the request information or not upon each receipt, and assigns the requests to diagnosticians. The assignment work may be done manually by the person in charge while taking the fortes of the diagnosticians into consideration. Alternatively, the assignment work may be done automatically on the basis of pre-entered information on the fortes of the diagnosticians, radiological interpretation schedule, and the like.

Using one of terminals 113 installed in the radiological interpretation center 151 (or home terminal 114 installed in diagnostician's house 153), a diagnostician whose job is radiological interpretation downloads, from the external storage device 117, the image data corresponding to the radiological interpretation request assigned by the person in charge, and conduct a radiological interpretation by reading it. After that, the diagnostician prepares a report containing radiological interpretation result information by using an application (not illustrated) running on the interpretation terminal 113 (or 114). A work server 105 processes the report transmitted from the said terminal of the diagnostician. The report after the processing is stored into the database 108. The radiological interpretation result information is stored in the database 108 in association with the request information. For example, the database 108 may include a storage unit configured to store the request information and the radiological interpretation result information in association with patient information. That is, the radiological interpretation result information is managed in a state in which the requesting facility information and the patient information can be found and determined on the basis of it. Though the terminals installed in the radiological interpretation center and the home terminal of the diagnostician are described as the interpreter-side terminals, they may be installed anywhere. The diagnostician may use a mobile terminal, etc. for reading the image away from the installed terminal.

Users including the person in charge of requesting for radiological interpretation at the requesting facility 150, the person in charge at the radiological interpretation center 151, and diagnosticians can exchange messages with one another by using a message function provided by the work server 105. Using the message function, a diagnostician can consult with, or exchange views with, other diagnostician about the content of radiological interpretation for a patient. Moreover, the message function can be used for communication between the person in charge at the requesting facility and the person in charge at the radiological interpretation center about schedule or consultation about the result of radiological interpretation. If the content of such a message pertains to a particular patient, in the database 108, the message history is managed in association with the patient information. It may be managed in association with not only the patient information but also the particular request information and/or report. The exchange of messages is processed by the work server 105 and managed in the database 108 in a unit called as "thread", which is a unit for grouping messages under a title for participants. A more detailed explanation of it will be given later.

For the purpose of follow-up monitoring of a particular patient, each user of the remote radiological interpretation system is allowed to request, via the terminal, for timeline screen display so as to visualize the examination history of the patient in time series. Accepting the request for timeline screen display via the terminal, the work server 105 gathers information with the use of which a timeline screen can be generated at the terminal side, and transmits the gathered information to the terminal, wherein the request information and the radiological interpretation result information (report information) pertaining to the corresponding patient managed in the database 108 are used for it. The terminal generates a timeline screen for display by using the received information.

Figure 2:
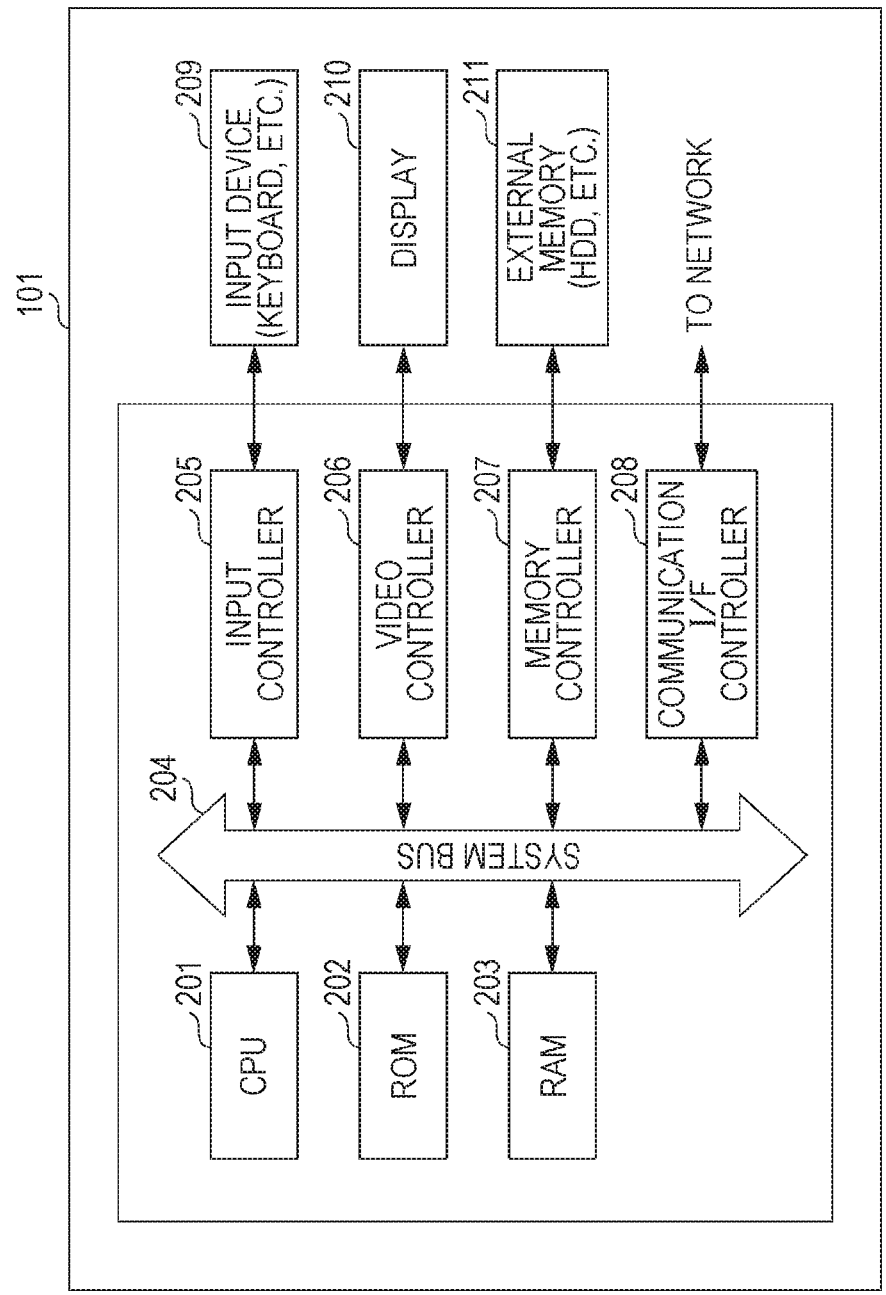
FIG. 2 is a diagram that illustrates an example of hardware configuration of an information processing apparatus according to an exemplary embodiment.

FIG. 2 is a diagram that illustrates the hardware configuration of an information processing apparatus such as various servers and terminals. A CPU 201 controls various devices and controllers connected to a system bus 204 integrally. In addition to BIOS (Basic Input Output System) and OS (Operating System), various programs, etc. for realizing various terminal functions are stored in a ROM 202 or an external memory 211.

A RAM 203 functions as the main memory and work area, etc. of the CPU 201. The CPU 201 loads programs necessary for processing, etc. out of the ROM 202 or the external memory 211 into the RAM 203 and runs the programs, thereby realizing various kinds of operation. An input controller 205 controls an input from an input device 209, for example, a keyboard and a pointing device (not illustrated) such as a mouse. A video controller 206 controls display on a display 210.

A memory controller 207 controls an access to the external memory 211, in which various data are stored. Examples of the external memory 211 are: an external storage device (HD), a flexible disk (FD), and a Compact Flash (®) memory connected via an adapter to a PCMCIA card slot. A communication I/F controller 208 controls connection to and communication with an external device via a network (for example, the network 115 illustrated in FIG. 1). Under the control of the communication I/F controller 208, for example, TCP/IP communication can be performed.

Various programs for realizing the operation of an embodiment of the present invention are stored in the external memory 211 and are run by the CPU 201 after loading into the RAM 203 when necessary. Various information tables and definition files, etc. necessary for running programs are also stored in the external memory 211. A more detailed explanation of them will be given later.

Functional Configuration

Figure 3:
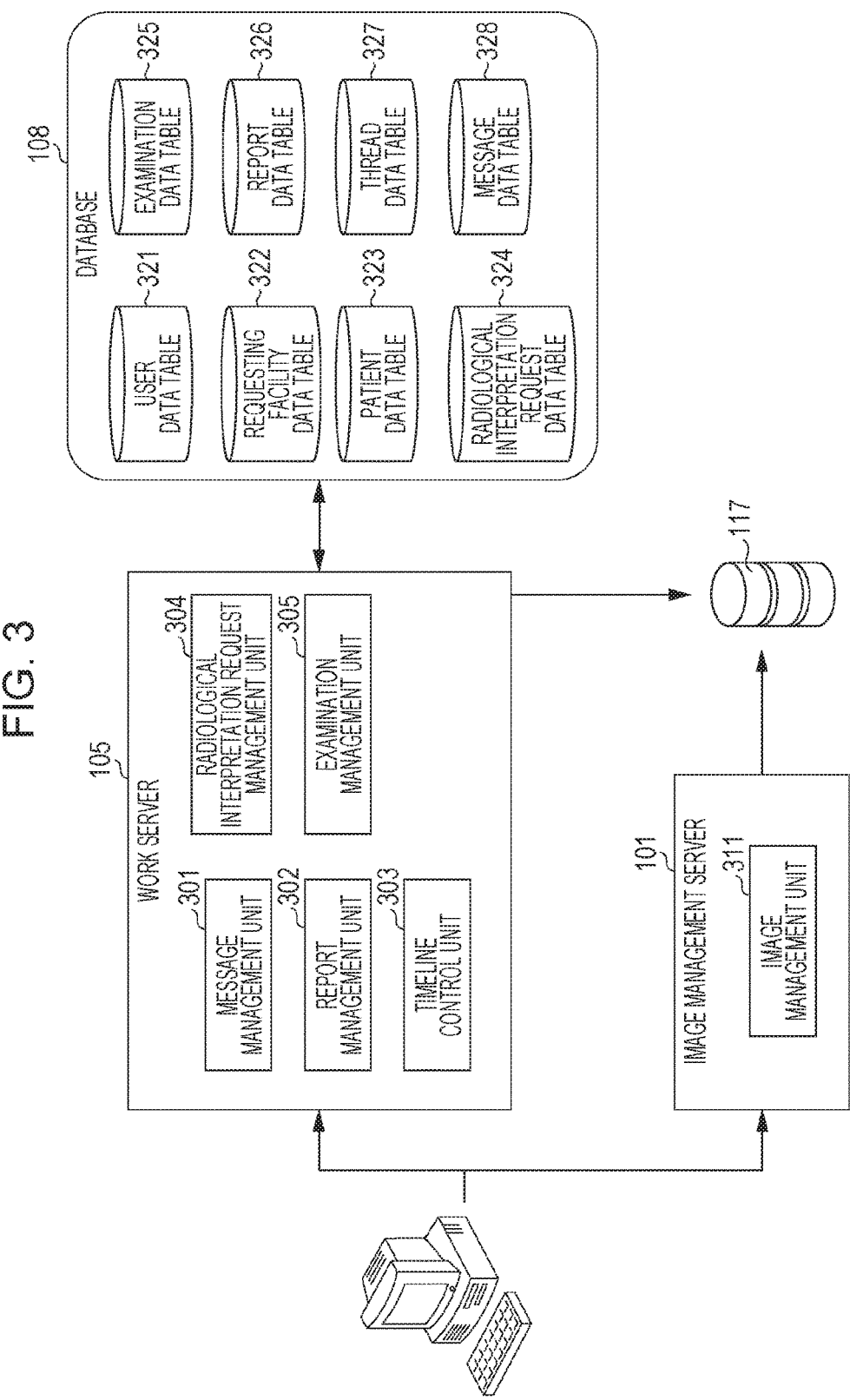
FIG. 3 is a diagram that illustrates an example of functional configuration of an information processing system according to an exemplary embodiment.

FIG. 3 is a diagram for explaining the functional configuration of servers according to the present embodiment.

The terminal used by each user is connected via the communication network 115, as described earlier, to the work server 105 and the image management server 101. The database 108, which is looked up by the work server 105, contains a user data table 321, a requesting facility data table 322, a patient data table 323, a radiological interpretation request data table 324, an examination data table 325, a report data table 326, a thread data table 327, and a message data table 328.

The image management unit 311 of the image management server 101 issues and assigns a unique ID (identification information) to each piece of image data transmitted from the modality 111 via the image relaying client 110. The ID-assigned data is stored into the external storage device 117. When it is stored, the examination management unit 305 of the work server 105 updates the examination data table 325 stored in the database 108.

Upon receipt of a request from the requesting terminal 109, the radiological interpretation request management unit 304 of the work server 105 analyzes the request and updates the patient data table 323 and the radiological interpretation request data table 324 stored in the database 108.

Upon receipt of a report from the terminal of the designated diagnostician, the report management unit 302 of the work server 105 processes it for storage into the external storage device 117, and updates the radiological interpretation result data table stored in the database 108.

The message management unit 301 of the work server 105 processes the thread of messages exchanged between users, and updates the thread data table 327 stored in the database 108, in which the thread associated with the patient information is managed. The message management unit 301 of the work server 105 manages each message associated with a thread by updating the message data table 328.

Upon receipt of instructions for timeline screen display from a user, the timeline control unit 303 of the work server 105 finds and determines the data corresponding to the specified patient information out of the tables stored in the database 108, and transmits the data to the terminal via which timeline screen display was instructed. By this means, the terminal can perform timeline screen display.

Data Tables

Next, with reference to FIGS. 9 and 10, an example of the data tables stored in the database 108 will now be explained.

Each entry in the user data table 321 illustrated in FIG. 9A is made up of user ID 901, user name 902, and user's role 903 managed in the remote radiological interpretation system. These items of entry are set for each user who is permitted to log in to the system. Portal page display content that differs depending on the role 903 may be presented.

The requesting facility data table 322 illustrated in FIG. 9B is for registration of information on requesting facilities in the remote radiological interpretation system. Each entry in this table is made up of requesting facility ID 911 and requesting facility name 912.

The patient data table 323 illustrated in FIG. 9C is a table into which patient data contained in radiological interpretation request information is added one after another. Each entry in this table is made up of requesting facility ID 921, patient ID 922, patient name 923, and patient birth date 924.

The radiological interpretation request data table 324 illustrated in FIG. 9D is a table into which request content in radiological interpretation request information is added one after another. Each entry in this table is made up of request ID 931, which is assigned to each request, requesting facility ID 932, patient ID 933, request date 934, examination ID 935, examination type 936, examined region of body 937, request status 938, and request receptionist user 939, which shows the person in charge at the radiological interpretation center.

Each entry in the examination data table 325 illustrated in FIG. 10A is made up of examination UID 1001 for the examination corresponding to the request information, examination date 1002, modality type 1003, requesting facility ID 1004, patient ID 1005, and image ID 1006.

The report data table 326 illustrated in FIG. 10B is a table for management of report information prepared by diagnosticians. Each entry in this table is made up of report ID 1011, requesting facility ID 1012, request ID 1013, patient ID 1014, report status 1015, diagnostician in charge 1016, radiological interpretation date 1017, target region of body 1018, and radiological interpretation result 1019.

Each entry in the thread data table 327 illustrated in FIG. 10C is made up of thread ID 1021, thread title 1022, thread owner 1023, participants 1024, requesting facility ID 1025, and patient ID 1026.

Each entry in the message data table 328 illustrated in FIG. 10D is made up of message ID 1031, thread ID 1032, message sender user name 1033, transmission date 1034, and message text 1035, which is the content of a message.
Processing Flow Next, with reference to the flowcharts of FIGS. 4 to 8, a series of processing ending with timeline screen display will now be explained.

The CPU of each of the information processing apparatuses (109, 112, 113, and 114), which is a client terminal capable of making a request for timeline screen display, and of the work server 105, reads out and executes programs stored in the corresponding storage. For example, the CPU of the information processing apparatuses may include a receiving unit configured to receive a request for timeline screen display. The processing described below is realized as a result of program execution.

In S401, instructions for timeline screen display are given to the CPU 201 of an information processing apparatus by a user via a portal, with at least a patient specified by the user. Information on the patient is transmitted to the work server 105.

Figure 11A:
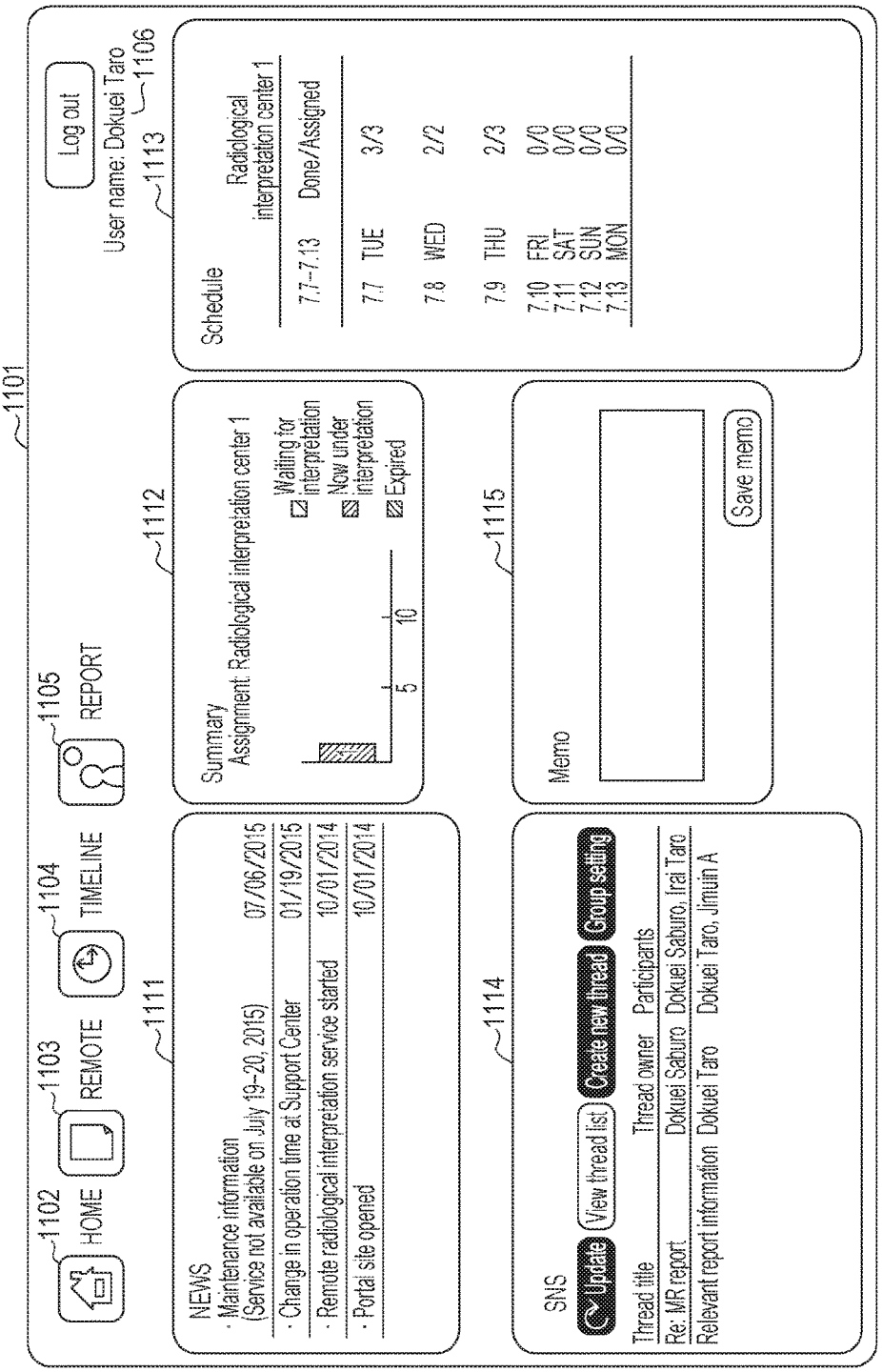
FIG. 11A is a diagram that illustrates an example of a screen that a remote radiological interpretation user can browse.

With reference to FIGS. 11A, 11B, 12, and 13, which show screen examples, three methods that a user can use for giving instructions for timeline screen display will now be explained. The differences in the content of timeline screen display described later arise from differences in the method of display instructions. FIG. 11A shows a portal page for giving instructions for timeline screen display, with the patient information specified. FIG. 12 shows a portal page for giving instructions for timeline screen display, with the patient information and the request information specified. FIG. 13 shows a report page for giving instructions for timeline screen display, with the patient information and the report information specified.

The portal page 1101 illustrated in FIG. 11A is an initial page that is displayed upon logon by a user whose name is "Dokuei Taro" 1106. The portal page 1101 has a HOME button 1102, which is a button for portal display, a remote radiological interpretation button 1103, which is a button for starting an assigned radiological interpretation task or for searching for the content of radiological interpretation reported by other diagnosticians, a timeline button 1104, which is a button for giving instructions for timeline screen display, and a report button 1105, which is a button for jumping to a report page.

In addition, the portal page 1101 has an information display box 1111, in which information received from the radiological interpretation center, etc. is displayed, a message box 1114, in which message threads whose participants include the user are displayed, a summary box 1112, the display content of which enables the user to confirm the status of assigned radiological interpretation tasks, a memorandum box 1115, in which the user can jot down notes to be stored, and a schedule box 1113, the display content of which enables the user to check the user's radiological interpretation schedule several days ahead.

Figure 11B:
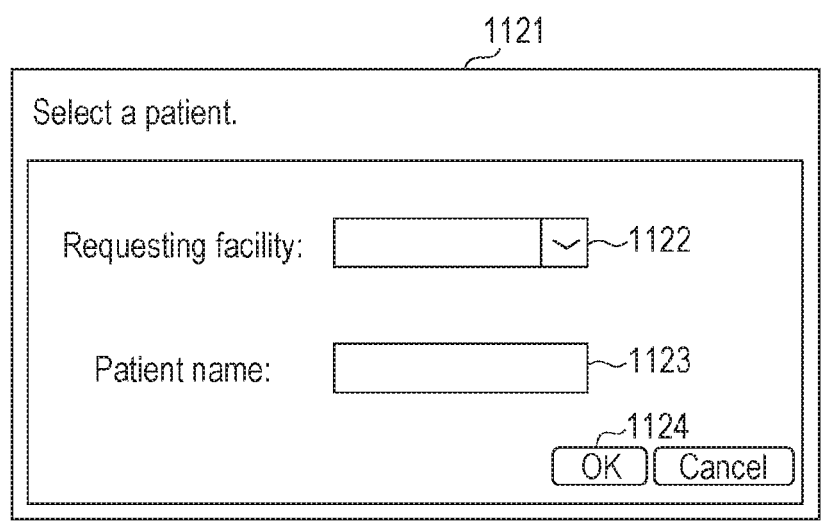
FIG. 11B is a diagram that illustrates an example of a window that prompts the user to make patient selection.

If the user clicks the timeline button 1104 on the portal page 1101 illustrated in FIG. 11A for giving instructions for timeline screen display, a patient selection window 1121 illustrated in FIG. 11B appears on the display screen. The user enters, regarding the patient for which the user demands timeline screen generation, requesting facility 1122 and patient name 1123, and next clicks an OK button 1124. In this way, the user can give instructions for timeline screen display, with the patient information specified. The request input is not essential. It is sufficient as long as the patient is specified.

The page 1201 illustrated in FIG. 12 appears on the display screen if the remote radiological interpretation button 1103 on the portal page 1101 illustrated in FIG. 11A is clicked. On the page 1201, the user enters various conditions and next clicks a "Search" button 1205. As a result, content that satisfies the entered conditions is retrieved from the radiological interpretation request data table 324 stored in the database 108. The retrieved content is displayed on the display screen. The example of FIG. 12 shows search results displayed when the "Search" button 1205 is clicked by the user after the selection of "Interpretation done".

The display on the display screen includes a radiological interpretation status column 1211, a request column 1212, in each cell of which an icon for browsing the content of a request is displayed, an image column 1213, in each cell of which an icon for starting a medical image viewer is displayed, a remarks column 1214, in each cell of which an icon for starting a report viewer for browsing remarks is displayed, a timeline column 1215 for timeline screen display instructions, a requester column 1216, each cell of which shows requesting facility, a patient ID column 1217, a patient name column 1218, an age column 1219, a gender column 1220, an examination type column 1221, an examined region of body column 1222, and a request time and date column 1223.

To give instructions for timeline screen display from the page 1201 illustrated in FIG. 12, the user clicks the timeline icon of the radiological interpretation request of interest, which the user wants to be displayed, in the timeline column 1215. In this way, instructions for timeline screen display are given, with the patient information and the request information specified.

The report page 1301 illustrated in FIG. 13 appears on the display screen if the report button 1105 on the portal page 1105 illustrated in FIG. 11A is clicked. As a work list, report information on radiological interpretation which the login diagnostician is in charge of is retrieved from the report data table 326 and is displayed. S/he selects report information for which s/he wants to enter remarks from the work list and clicks an "Enter remarks" button 1341. An input screen (not illustrated) for the report is started up. If a "Display image" button 1342 is clicked after the selection of report information from the work list, the viewer for displaying the medical image corresponding to the report information is started up. If a "Timeline" button 1343 is clicked after the selection of report information from the work list, instructions for timeline screen display are given, with the patient information and the report information specified. If a "Return" button 1344 is clicked after the selection of report information from the work list, the report is returned as filled-in one to the radiological interpretation center.

The login diagnostician can search for a report(s) on a patient(s) who is not in his/her charge by entering requesting facility name 1322, patient ID 1323, and patient name 1324 in the respective fields of a search area 1321 on the report page 1301 and next clicking a "Search" button 1325. The search result is displayed in a search result display area 1331. Requesting facility ID 1332, patient ID 1333, request date 1334, examined region of body 1335, status 1336, and examined region of body 1337 are displayed in the search result display area 1331. In FIG. 13, a search example with the entry of "Kannon Hospital" in the requesting facility field is illustrated. If the "Display image" button 1342 is clicked in a state in which report information (for example, report information 1338) has been specified by the user, the viewer for displaying the medical image corresponding to the report information is started up. If the "Timeline" button 1343 is clicked, instructions for timeline screen display are given, with the patient information and the report information specified by the user.

Upon receipt of instructions for timeline screen display from the user via the portal as described above, the CPU 201 of the information processing apparatus transmits the received information to the work server 105.

In S402, the CPU 201 of the work server 105 accepts the instructions for timeline screen display, with the patient information specified, by receiving the instructions for timeline screen display from the information processing apparatus. For example, the CPU of the work server 105 may include an acceptance unit configured to accept a request for timeline screen display from the information processing apparatus.

In S403, the CPU 201 of the work server 105 determines threads that are relevant to the patient information accepted in S402 in the thread data table 327 and determines message information of the threads in the message data table 328. Necessary data is acquired from these tables. The acquired data is stored in the form of an event table illustrated in FIG. 14A, wherein the event table is generated in a memory of the work server 105. The event table is made up of time and date of event occurrence 1401, place of occurrence 1402, event class 1403, and display data 1404. Information of these constituents of the event table is acquired from the thread data table 327 and the message data table 328. For classification, "Message" is registered as the event class 1403.

In S404, the CPU 201 of the work server 105 acquires, from the examination data table 325, examination data that are relevant to the patient information accepted in S402, and stores the examination data into the event table generated in the memory of the work server 105. For the examination data, requesting facility name, which shows the name of the medical facility at which the examination was conducted on the patient, is registered as the place of occurrence 1402; the examination date is registered as the time and date of event occurrence 1401; "Examination conducted" is registered as the event class 1403. The content of the examination determined from the examination data table 325, and a typical image, etc. are registered as the display data 1404.

In S405, the CPU 201 of the work server 105 acquires, from the radiological interpretation request data table 324, request data that are relevant to the patient information accepted in S402, and stores the request data into the event table generated in the memory of the work server 105. For the radiological interpretation request data, requesting facility name is registered as the place of occurrence 1402; the request date is registered as the time and date of event occurrence 1401; "Request received" is registered as the event class 1403. The patient name, the examination type, and the examined region of body, etc. determined from the radiological interpretation request data table 324 are registered as the display data 1404.

In S406, the CPU 201 of the work server 105 acquires, from the report data table 326, report data that are relevant to the patient information accepted in S402, and stores the report data into the event table generated in the memory of the work server 105. For the report data, the radiological interpretation center is registered as the place of occurrence 1402; the radiological interpretation date is registered as the time and date of event occurrence 1401; "Results of radiological interpretation" is registered as the event class 1403. The name of the diagnostician who conducted radiological interpretation, the results of radiological interpretation, and the interpreted region of body, etc. are registered as the display data 1404.

Thus, the CPU 201 of the work server 105 may include a determination unit configured to determine the request information and the radiological interpretation result information associated with the patient information specified for the request received by the receiving unit. The sequential order of registration in S403 to S406 is not limited to the above example.

Figure 5:
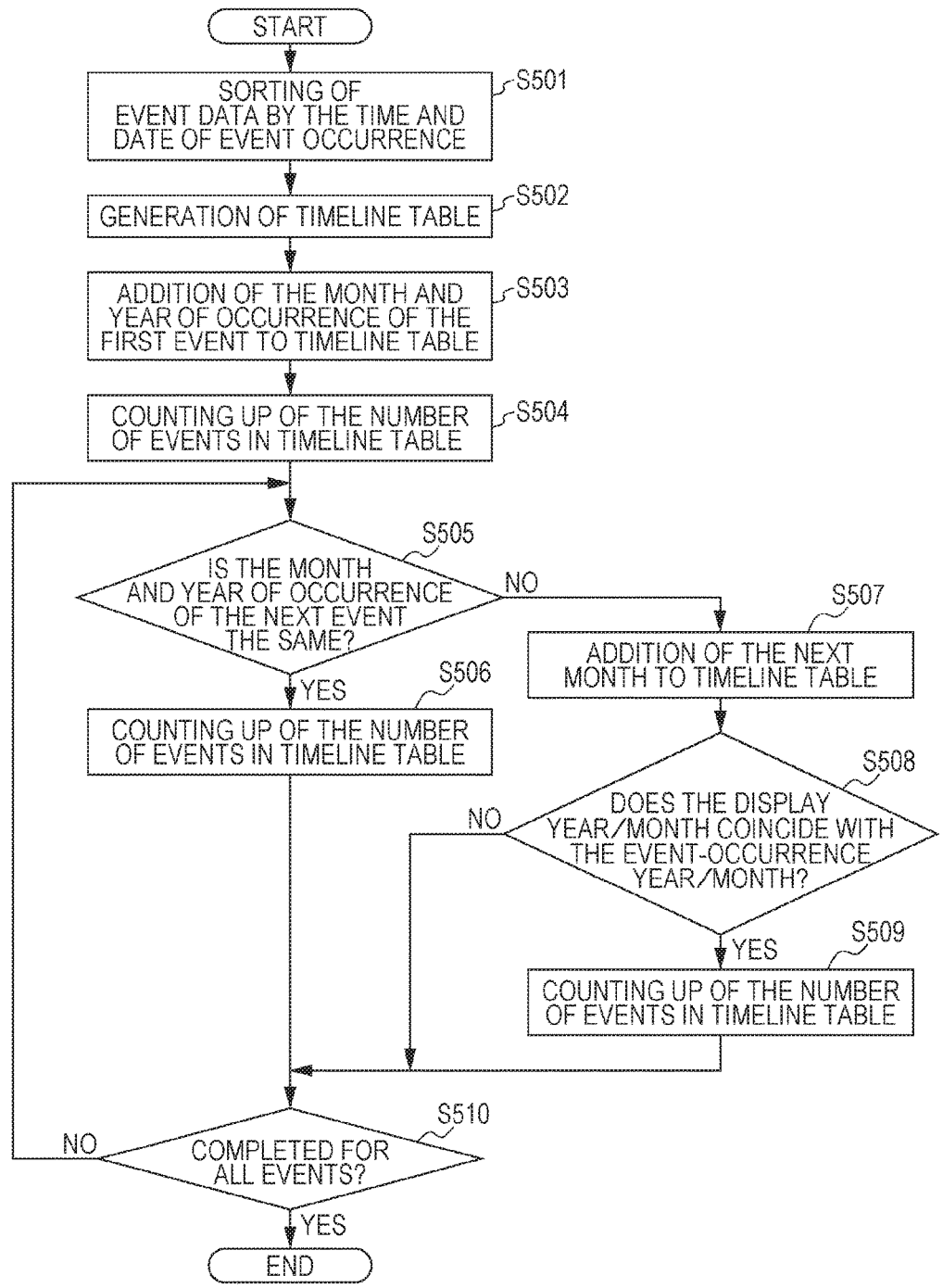
FIG. 5 is a flowchart for explaining the procedure of creation of timeline data.

In S407, the CPU 201 of the work server 105 creates timeline data by using the information registered in the event table. With reference to FIG. 5, the creation of timeline data in S407 will now be explained in detail.

In S501, the CPU 201 of the work server 105 sorts the event data registered in the event table by the time and date of event occurrence (time-and-date information).

In S502, the CPU 201 of the work server 105 generates a timeline table illustrated in FIG. 14B. The timeline table is made up of timeline display year/month 1411 and the number of events occurred 1412.

In S503, the CPU 201 of the work server 105 registers, into the timeline table, the month and year of occurrence of the first event registered in the event table.

In S504, the CPU 201 of the work server 105 counts up the number of events in the timeline table.

In S505, the CPU 201 of the work server 105 determines whether the month and year of occurrence of the next event registered in the event table is the same as the month and year of occurrence of the event having been registered last or not. If it is determined in S505 that the two are the same as each other, the process proceeds to S506. In S506, the number of events in the timeline table is counted up. If it is determined that the two are not the same as each other, the process proceeds to S507. In S507, the next month is added to the timeline table.

In S508, the CPU 201 of the work server 105 determines whether the display year/month added to the timeline table in S507 coincides with the month and year of occurrence of the event or not.

If it is determined in S508 that the two coincide with each other, the process proceeds to S509. In S509, the number of events in the timeline table is counted up. If it is determined that the two do not coincide with each other, the process proceeds to S510 without counting it up.

In S510, the CPU 201 of the work server 105 determines whether registration into the timeline table has been completed for all of the events registered in the event table or not. If it is determined that registration has not been completed for all of them yet, the process returns to S505 and continues. The process ends if it is determined that registration has been completed for all of them.

The foregoing is a description of the flowchart of FIG. 5.

Figure 4:
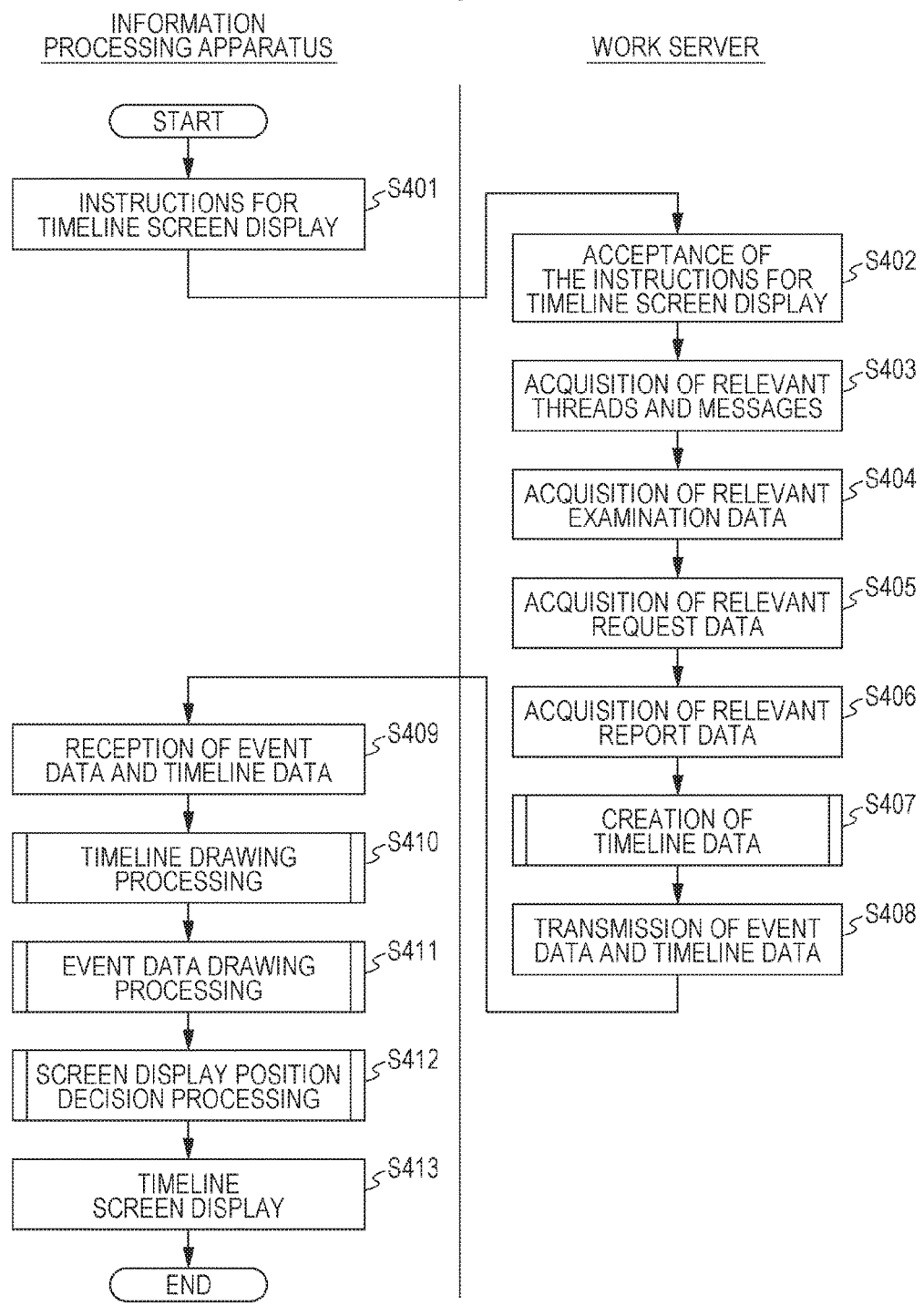
FIG. 4 is a flowchart for explaining the procedure of timeline screen display.

In S408 of FIG. 4, the CPU 201 of the work server 105 transmits information on the event table and information on the timeline table, which has been generated through the processing flow of FIG. 5, to the information processing apparatus. For example, the CPU 201 of the work server 105 may include a transmitting unit configured to transmit, to the information processing apparatus, the request information and the radiological interpretation result information.

In S409, the CPU 201 of the information processing apparatus receives the event data and the timeline data from the work server 105.

Figure 6:
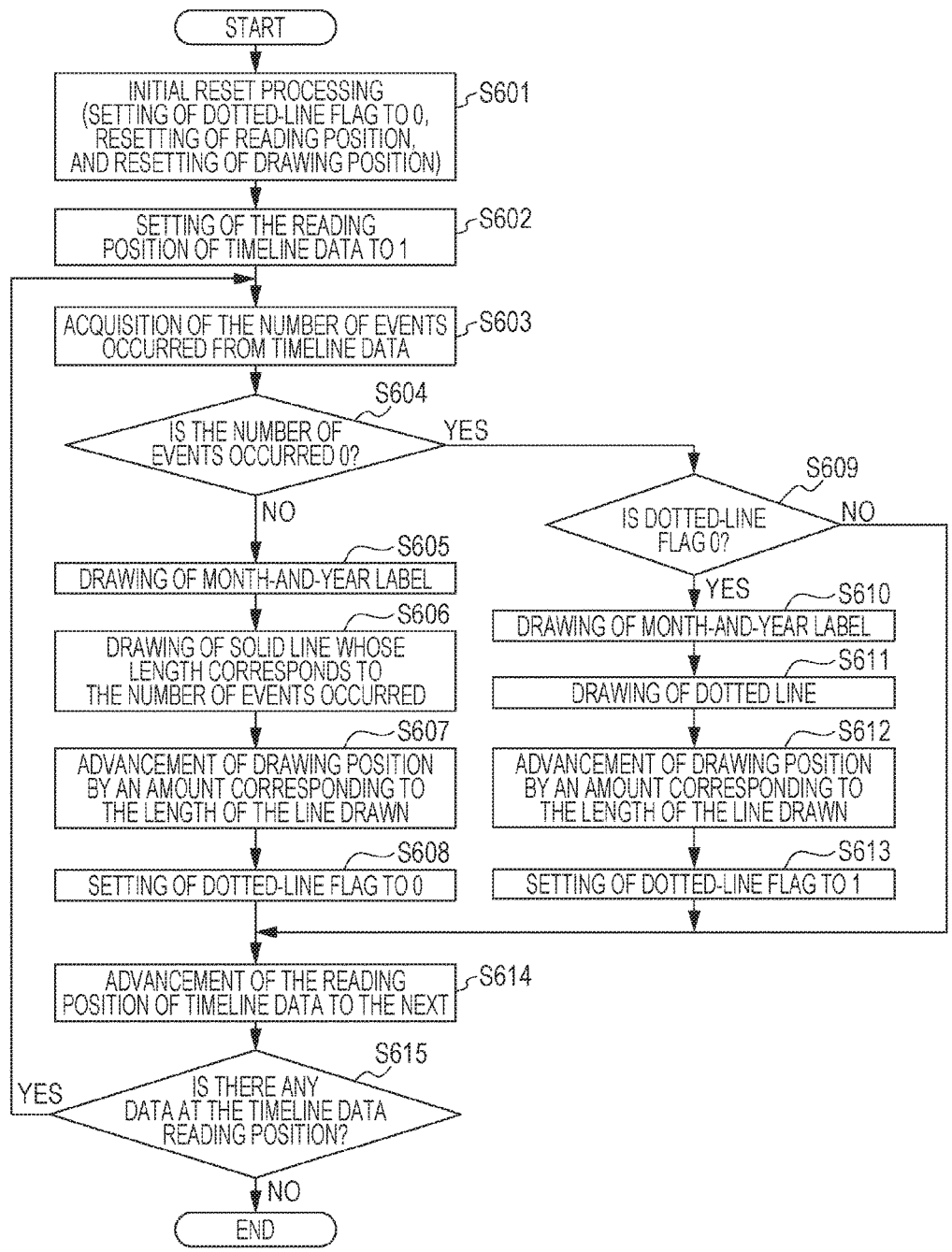
FIG. 6 is a flowchart for explaining the procedure of timeline drawing processing.

In S410, the CPU 201 of the information processing apparatus performs timeline drawing processing. With reference to FIG. 6, timeline drawing processing will now be explained in detail.

In S601, the CPU 201 of the information processing apparatus performs initial reset processing. Specifically, this processing includes: the setting of a dotted-line flag to 0, the resetting of a reading position, and the resetting of a drawing position.

In S602, the CPU 201 of the information processing apparatus sets the reading position of the timeline data to 1.

In S603, the CPU 201 of the information processing apparatus acquires the number of events occurred from the timeline data.

In S604, the CPU 201 of the information processing apparatus determines whether the number of events occurred acquired in S603 is 0 or not. If the number is determined to be not 0, the process proceeds to S605. In S605, a month-and-year label is drawn.

In 3606, the CPU 201 of the information processing apparatus draws a solid line (first timeline axis) whose length corresponds to the number of events occurred acquired in S603. That is, the solid line represents a time period for which information regarding radiological interpretation is stored.

In S607, the CPU 201 of the information processing apparatus advances the drawing position by an amount corresponding to the length of the line drawn in S606.

In S608, the CPU 201 of the information processing apparatus sets the dotted-line flag to 0, and the process proceeds to S614.

If it is determined in S604 that the number of events occurred is 0, the process proceeds to S609. In S609, it is determined whether the dotted-line flag is 0 or not.

If it is determined in S609 that the dotted-line flag is 0, the process proceeds to S610. In S610, the month-and-year label of the reading position is drawn.

In S611, the CPU 201 of the information processing apparatus draws a dotted line (second timeline axis) that has a predetermined length. That is, the dotted line indicates the existence of a time period for which no information regarding radiological interpretation is stored. The length of the dotted line may be either the same as or shorter than the length of the solid line corresponding to one event. This is because there is no event information displayed on the dotted line.

In S612, the CPU 201 of the information processing apparatus advances the drawing position by an amount corresponding to the length of the line drawn in S611.

In S613, the CPU 201 of the information processing apparatus sets the dotted-line flag to 1, and the process proceeds to S614.

If it is determined in S609 that the dotted-line flag is not 0 (that is, the dotted-line flag is 1), the process proceeds to S614.

In 3614, the CPU 201 of the information processing apparatus advances the reading position of the timeline data to the next.

In S615, the CPU 201 of the information processing apparatus determines whether there is any data at the timeline data reading position or not. The process ends if there is no data. The process returns to S603 and continues if there is some data.

Through the processing described above, screen content for displaying the timeline axes and the month-and-year labels on the timeline screen, that is, the timeline generated on the basis of the time-and-date information, is generated as interim result content. The foregoing is a description of the flowchart of FIG. 6.

Figure 7:
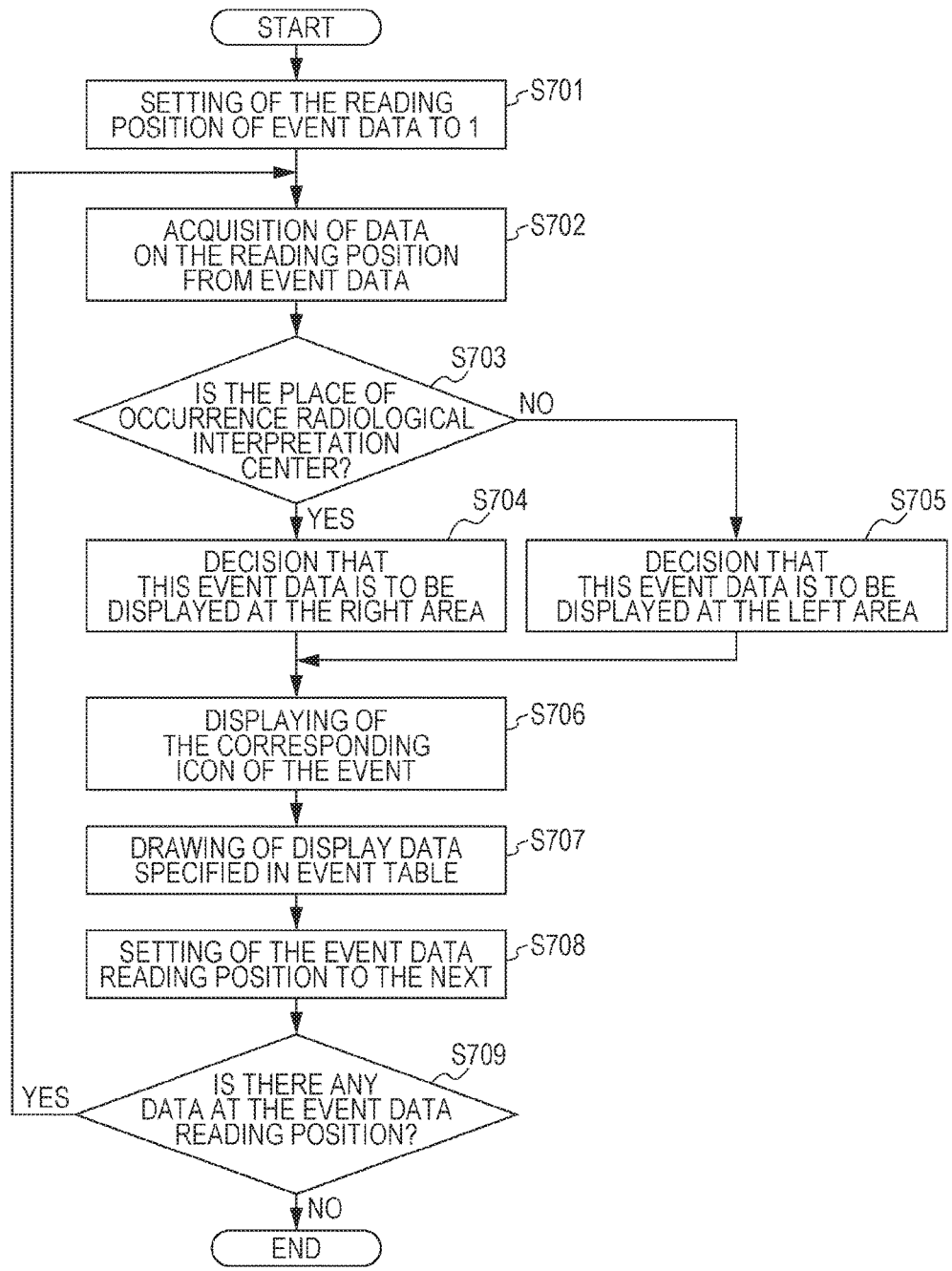
FIG. 7 is a flowchart for explaining the procedure of event data drawing processing.

In S411 of FIG. 4, the CPU 201 of the information processing apparatus performs processing for drawing the event data on the timeline screen generated through the processing described above with reference to FIG. 6. With reference to FIG. 7, event data drawing processing will now be explained in detail.

In S701, the CPU 201 of the information processing apparatus sets the reading position of the event data received in S409 to 1.

In S702, the CPU 201 of the information processing apparatus acquires data on the reading position set in S701 from the event data.

In S703, the CPU 201 of the information processing apparatus determines whether the place of occurrence is the radiological interpretation center or not.

If it is determined in S703 that the place of occurrence is the radiological interpretation center, the process proceeds to S704. In S704, the CPU 201 of the information processing apparatus decides that this event data is to be displayed at the right area with respect to the timeline axis. If it is determined in S703 that the place of occurrence is not the radiological interpretation center, the process proceeds to S705. In S705, the CPU 201 of the information processing apparatus decides that this event data is to be displayed at the left area with respect to the timeline axis.

In the area decision processing of the present embodiment, the radiological interpretation center corresponds to the right side with respect to the timeline axis. However, the radiological interpretation center may correspond to the left side with respect to the timeline axis. Alternatively, instead of separation to the left side and the right side, the display area may be split into an upper part and a lower part. That is, the only thing needed in the above decision is that, when the display position of event information whose place of occurrence registered in the event table is a requesting-facility-side location is decided to be inside one of display areas separated from each other by a timeline axis, the display position of event information whose place of occurrence registered in the event table is a radiological-interpretation-side location should be decided to be inside the other of the display areas.

Since the events are displayed in these different areas with respect to the timeline axis depending on the place of occurrence each, the user can understand the event time series including the request at a glance on the timeline screen showing the medical history of the patient.

In S706, the CPU 201 of the information processing apparatus displays the corresponding icon of the event at the corresponding position on the timeline axis.

Figure 15:
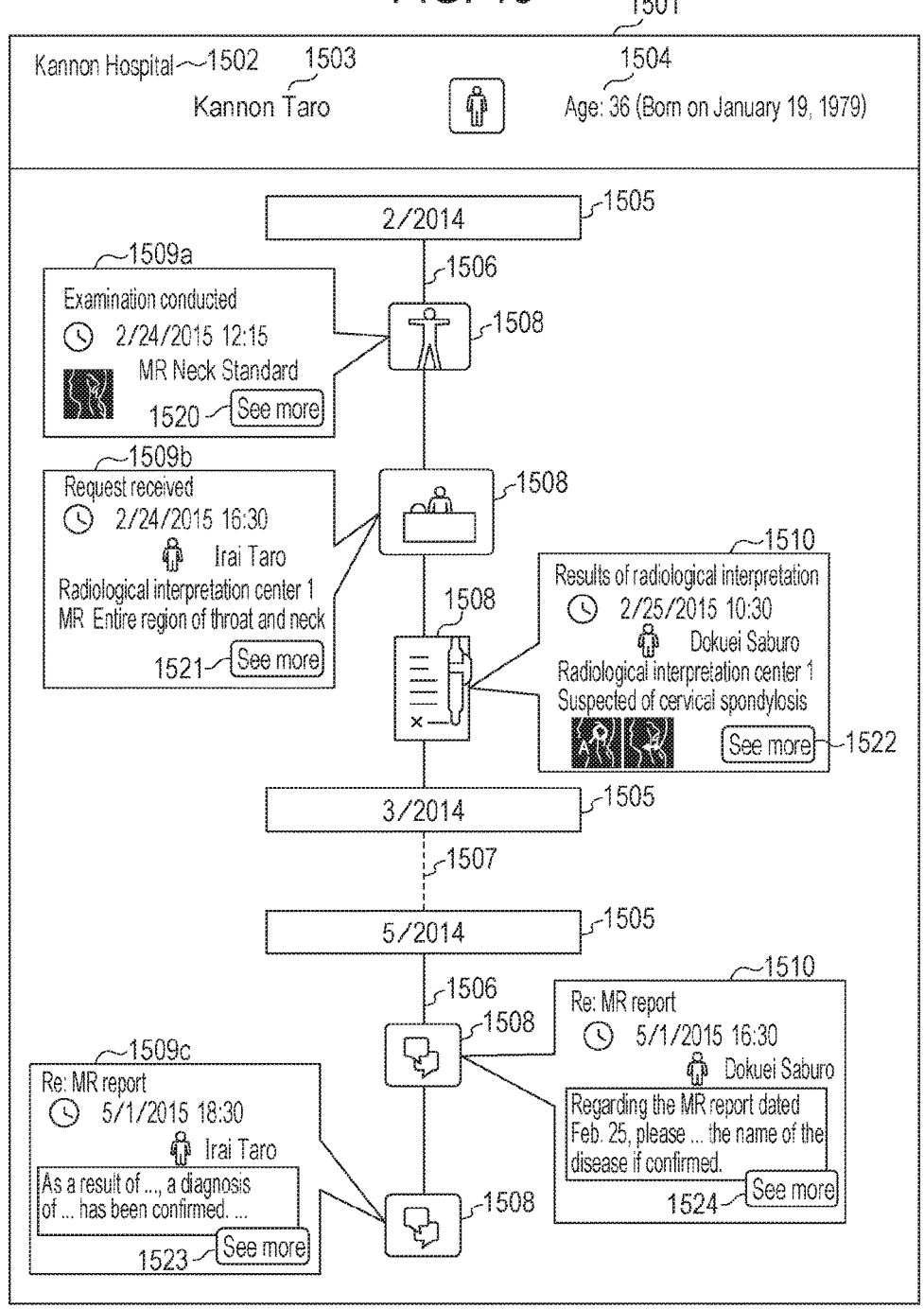
FIG. 15 is a diagram that illustrates an example of a timeline screen displayed when a request for display is made, with patient information specified.

Specifically, an icon 1508 illustrated in FIG. 15 is displayed on a solid-line timeline axis 1506. It may be displayed near the timeline axis 1506 instead of on-the-axis display.

In S707, at the position decided in S704 or S705, the CPU 201 of the information processing apparatus draws the display data specified in the event table. Specifically, if the place of occurrence is the requesting facility, as in a timeline screen 1501 illustrated in FIG. 15, event information 1509*a*, 1509*b*, 1509*c* is displayed at the left side with respect to the timeline axis. If the place of occurrence is the radiological interpretation center, event information 1510 is displayed at the right side with respect to the timeline axis.

In S708, the CPU 201 of the information processing apparatus sets the event data reading position to the next.

In S709, the CPU 201 of the information processing apparatus determines whether there is any data at the event data reading position or not. The process ends if there is no data. The process returns to S702 and continues if there is some data.

Through the processing described above with reference to FIG. 7, drawing information that is to be used for displaying the timeline screen including the timeline axes 1506 and 1507 and the event information 1509 and 1510 illustrated in FIG. 15 is generated.

Next, in S412, the CPU 201 of the information processing apparatus performs processing for deciding a screen display position. With reference to FIG. 8, screen display position decision processing will now be explained in detail.

In S801, the CPU 201 of the information processing apparatus determines whether the timeline screen display instructions given in S401 are instructions given with examination information specified in addition to patient information or not. Specifically, in a case where the user made the request for timeline screen display by selecting an icon in the timeline column 1215 illustrated in FIG. 12, it is determined that the timeline screen display instructions given in S401 are instructions given with examination information specified.

If it is determined in S801 that the timeline screen display instructions given in S401 are instructions given with examination information specified, the process proceeds to S802. In S802, the CPU 201 of the information processing apparatus draws icons 1602 and 1603 in an icon area 1601, which is an area for jumping to other examination data of the same patient. The icon 1602 is for jumping to past similar requests. The icon 1603 is for jumping to recent similar requests.

Figure 16:
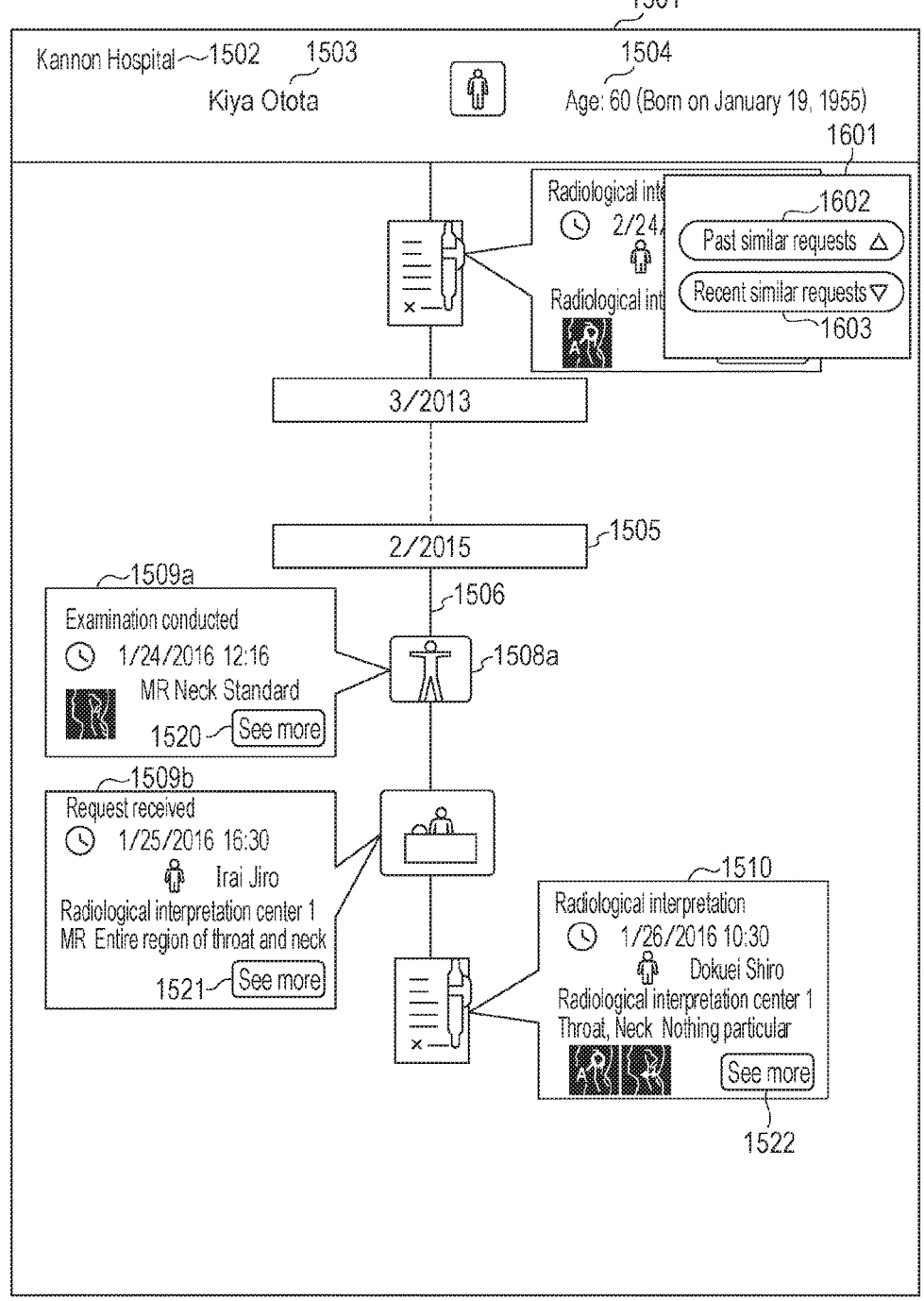
FIG. 16 is a diagram that illustrates an example of a timeline screen displayed when a request for display is made, with patient information and examination information specified.

FIG. 16 is a diagram of a timeline screen displayed when timeline screen display is requested with examination information specified.

In S803, the CPU 201 of the information processing apparatus decides a display position in such a way as to make the examination icon viewable, for example, as illustrated in FIG. 16, an examination icon 1508*a* at the center of the timeline screen 1501. The only thing needed is that the examination icon is viewable; displaying it at the center is not essential.

If it is determined in S801 that the timeline screen display instructions given in S401 are not instructions given with examination information specified, the process proceeds to S804. In S804, it is further determined whether the above-mentioned timeline screen display instructions are instructions given with report information specified or not.
Specifically, in a case where the user made the request for timeline screen display by clicking the "Timeline" button 1343 illustrated in FIG. 13 after the selection of report information, it is determined that the above-mentioned timeline screen display instructions are instructions given with report information specified.

If it is determined in S804 that the above-mentioned timeline screen display instructions are instructions given with report information specified, the process proceeds to S805. In S805, the CPU 201 of the information processing apparatus draws the icon 602, which is for jumping to past similar requests, and the icon 603, which is for jumping to recent similar requests, in the icon area 1601, which is an area for jumping to other examination data of the same patient.

Figure 17:
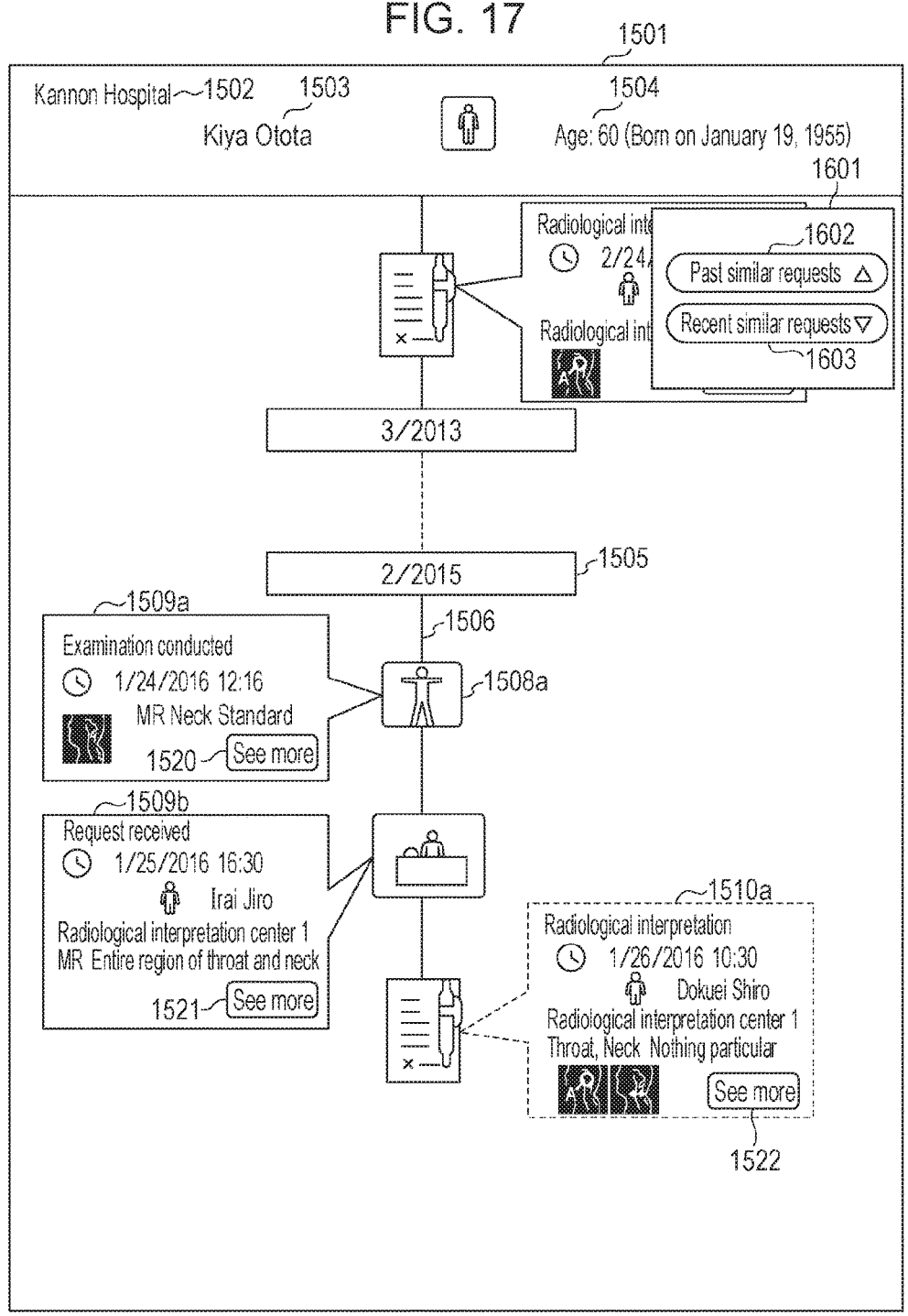
FIG. 17 is a diagram that illustrates an example of a timeline screen displayed when a request for display is made, with patient information and report information specified.

FIG. 17 is a diagram of a timeline screen displayed when timeline screen display is requested with report information specified.

In S806, the CPU 201 of the information processing apparatus decides a display position in such a way as to make the examination icon viewable, for example, as illustrated in FIG. 17, the examination icon 1508*a* at the center of the timeline screen 1501. The only thing needed is that the examination icon is viewable; displaying it at the center is not essential.

In S807, the CPU 201 of the information processing apparatus performs processing for highlight display of event information 1510*a* on the results of radiological interpretation. Then, the process ends. Specifically, it is possible to perform highlight display by enclosing the content of the event information 1510*a* in, for example, a dashed line box as illustrated in FIG. 17.

If it is determined in S804 that the above-mentioned timeline screen display instructions are not instructions given with report information specified, the process proceeds to S808. Specifically, the process proceeds to S808 in a case where the user made the request for timeline screen display by clicking the timeline button 1104 on the portal page 1101 illustrated in FIG. 11A.

In S808, the CPU 201 of the information processing apparatus decides a display position for chronological display starting with the most previous examination of the patient, or for reverse-chronological display starting with the latest examination of the patient. Then, the process ends.

Through the processing described above with reference to FIG. 8, a drawing position for displaying the timeline screen including the timeline axes 1506 and 1507 and the event information 1509 and 1510 illustrated in FIGS. 15, 16, and 17 on the display screen is determined.

In S413, the CPU 201 of the information processing apparatus causes the display device to display the timeline screen at the drawing position determined in S412 (display control). For example, the CPU 201 of the information processing apparatus may include a display control unit configured to perform control for generation of a timeline screen.

On the timeline screen 1501 illustrated in FIGS. 15, 16, and 17, a "See more" button may be provided in the area of each piece of event information. Specifically, for example, in preferred implementation of the embodiment, when a "See more" button 1520 provided in the area of "Examination conducted" event information is clicked, the viewer for displaying the medical image corresponding to the examination is started up. Preferably, when a "See more" button 1521 provided in the area of "Request received" event information is clicked, a request information viewer screen (not illustrated) should be displayed. Preferably, when a "See more" button 1522 provided in the area of "Results of radiological interpretation" event information is clicked, the report page viewer should be started up. Preferably, when a "See more" button 1523 or 1524 provided in the area of "Message" event information is clicked, a message viewer screen (not illustrated), which enables the user to read the whole text of the message, should be displayed.

The basic information of the patient such as requesting facility name 1502, patient name 1503, and age 1504 may be displayed at the header of the timeline screen 1501.

A series of processing ending with timeline screen display has been explained with reference to the flowcharts of FIGS. 4 to 8 in the present embodiment. In a system for managing requests for radiological interpretation of medical images and managing the results of radiological interpretation conducted on the basis of the requests, the disclosed technique makes it possible to generate an easy-to-view timeline screen for visualization of the medical history of a patient, which is achieved by displaying event information pertaining to the requester side (requester-side event information) at one of display areas separated from each other by a timeline axis and by displaying event information pertaining to the interpreter side (interpreter-side event information) at the other of the display areas.

Moreover, since a drawing position for the drawing of a timeline screen and conditions for highlight display on the timeline screen are set depending on which kind of information was added to the patient information when the request for timeline screen display was made, the disclosed technique makes it easier for a user to visually recognize an event of user's interest, etc. in the displayed medical history.

In the control example of the present embodiment, the work server 105 finds and determines necessary information out of each table stored in the database 108, and transmits, to the terminal, the data necessary for timeline screen generation at the terminal side. The terminal generates a timeline screen on the basis of the received data. Instead of generation at the terminal side, a timeline screen may have been generated at the work-server side in advance, and it may be transmitted to the terminal for display on the display screen of the terminal.

The present invention can be embodied in various modes of implementation, for example, as a system, as an apparatus, as a method, as a program, or as a storage medium. Specifically, for example, the present invention may be applied to a system including a plurality of devices, or may be applied to an apparatus including only one device.

The present invention encompasses a software program that makes it possible to implement the functions of the foregoing embodiment via direct code supply to a system or an apparatus, or remote code supply. Implementing the functions by reading and executing the supplied program code by an information processor of the system or the apparatus is also within the scope of the present invention.

Therefore, a program code itself installed in an information processing apparatus in order to implement, on the information processing apparatus, functions and processes according to aspects of the present invention also embodies the present invention. In other words, a computer program itself for implementing functions and processes according to aspects of the present invention is also within the scope of the present invention.

The program may have any form such as object code, a program executed by an interpreter, or script data supplied to OS, as far as it functions as a program.

Examples of a recording medium for supplying the program include: a flexible disk, a hard disk, an optical disk, a magneto-optical disk (MO), a compact-disc read-only memory (CD-ROM), a compact-disc recordable (CD-R), and a compact-disc rewritable (CD-RW). Other examples include a magnetic tape, a non-volatile memory card, a ROM, and a digital versatile disc (DVD including DVD-ROM and DVD-R).

Another example of a method for supplying the program is as follows. A connection to a homepage is established over the Internet by using a browser on a client computer. A computer program according to aspects of the present invention can be supplied by downloading the program itself from the homepage or by downloading a file containing the compressed program with an auto-install function to a recording medium such as a hard disk.

As another mode of implementation, the foregoing functions and processes according to aspects of the present invention may be implemented by dividing a set of program codes constituting a program according to aspects of the present invention into a plurality of files, and by downloading these files from different homepages. In other words, a World Wide Web (WWW) server that enables a plurality of users to download a program file for implementing, with an information processing apparatus, functions and processes according to aspects of the present invention is also within the scope of the present invention.

As still another mode of implementation, the foregoing functions and processes according to aspects of the present invention may be implemented as follows. A program according to aspects of the present invention is encrypted. The encrypted program is stored into a storage medium such as a CD-ROM, and is distributed to users. A user who satisfies predetermined conditions is permitted to download key information for decrypting the encrypted program from a homepage via the Internet. Using the downloaded key information, the user can decrypt the encrypted program and install the decrypted program in an information processing apparatus, thereby implementing the functions and processes.

Alternatively, the foregoing functions and processes according to aspects of the present invention may be implemented by, by an information processing apparatus, execution of a program that has been read out. Alternatively, in accordance with the instructions of the program, OS running on the information processing apparatus, for example, may perform a part or the whole of actual processing, thereby implementing the functions and processes.

As still another mode of implementation, the foregoing functions and processes according to aspects of the present invention may be implemented as follows. A program read out of a recording medium is written into a memory mounted on a function expansion board inserted in an information processing apparatus or mounted on a function expansion unit connected to an information processing apparatus. After that, in accordance with the instructions of the program, a CPU included in the function expansion board or the function expansion unit may perform a part or the whole of actual processing, thereby implementing the functions and processes.

The foregoing embodiment is a mere example for implementation of aspects of the present invention. The foregoing embodiment shall not be construed to limit the technical scope of the present invention. That is, the present invention can be embodied in various ways without departing from its technical concept and its main features.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-152066, filed Jul. 31, 2015 which is hereby incorporated by reference herein in its entirety.

What is claimed is:

1. A remote interpretation system for management of an interpretation request sent from a requesting facility and management of an interpretation result corresponding to the interpretation request, comprising at least one processor and memory coupled to each other and cooperating to act as:
- an obtaining unit configured to obtain the interpretation request associated with a particular patient from among a plurality of interpretation requests associated with a plurality of patients and obtain the interpretation result corresponding to the interpretation request associated with the particular patient from among a plurality of interpretation results associated with the plurality of patients;
- a generating unit configured to generate a screen including a first region and a second region divided by a line representing a time axis; and
- an arrangement unit configured to arrange event data corresponding to the interpretation request in the first region in chronological order along the time axis and arrange event data corresponding to the interpretation result in the second region in chronological order along the time axis.

2. The remote interpretation system according to claim 1, wherein the obtaining unit obtains message information, which is sent from at least one of the requesting facility and an interpreter conducting interpretation according to the interpretation request sent from the requesting facility; and
wherein the arrangement unit arranges event data corresponding to the message information sent from the requesting facility in the first region in chronological order along the time axis and arranges event data corresponding to the message information sent from the interpreter in the second region in chronological order along the time axis.

3. The remote interpretation system according to claim 1, wherein the at least one processor and memory further cooperate to act as:
- a receiving unit configured to receive a request for the screen display, with the particular patient specified.

4. The remote interpretation system according to claim 1, wherein the at least one processor and memory further cooperate to act as:
- a display control unit configured to cause a display unit to display the screen on which the event data is arranged.

5. The remote interpretation system according to claim 1, wherein the arrangement unit arranges an icon corresponding to the event data on the line representing the time axis in chronological order.

6. The remote interpretation system according to claim 1, wherein the first region and the second region are regions located on left and right or upper and lower side of the line representing time axis.

7. A control method of a remote interpretation system for management of an interpretation request sent from a requesting facility and management of an interpretation result corresponding to the interpretation request, comprising:
- obtaining the interpretation request associated with a particular patient from among a plurality of interpretation requests associated with a plurality of patients and obtaining the interpretation result corresponding to the interpretation request associated with the particular patient from among a plurality of interpretation results associated with the plurality of patients;
- generating a screen including a first region and a second region divided by a line representing a time axis; and
- arranging event data corresponding to the interpretation request in the first region in chronological order and arranging event data corresponding to the interpretation result in the second region in chronological order.

8. A remote interpretation system comprising at least one processor and memory coupled to each other and cooperating to act as:
- an obtaining unit configured to obtain event data related to an interpretation associated with a particular patient from among a plurality of interpretations associated with a plurality of patients;
- a generating unit configured to generate a screen including a first region and a second region divided by a line representing a time axis;
- an arrangement unit configured to arrange, in chronological order, the obtained event data in a region corresponding to a facility related to the obtained event data, from among the first region and the second region.

9. The remote interpretation system according to claim 8, wherein, in a case where the obtained event data is related to a requesting facility, the arrangement unit arranges the obtained event data in the first region in chronological order,
wherein, in a case where the obtained event data is related to an interpretation facility, the arrangement unit arranges the obtained event data in the second region in chronological order.

10. The remote interpretation system according to claim 8,
wherein the event data is at least one of information related to an interpretation request, information related to an interpretation result, and messages sent between a requesting facility and an interpretation facility.

11. The remote interpretation system according to claim 8, wherein the at least one processor and memory further cooperate to act as:
- a display control unit configured to cause a display unit to display the screen on which the obtained event data is arranged.

12. The remote interpretation system according to claim 8,
wherein the arrangement unit arranges an icon corresponding to the event data on the line representing the time axis in chronological order.

13. The remote interpretation system according to claim 8,
wherein the first region and the second region are regions located on left and right or upper and lower side of the line representing time axis.

14. A control method of a remote interpretation system comprising:
- obtaining event data related to an interpretation associated with a particular patient from among a plurality of interpretations associated with a plurality of patients;
- generating a screen including a first region and a second region divided by a line representing a time axis;
- arranging, in chronological order, the obtained event data in a region corresponding to a facility related to the obtained event data, from among the first region and the second region.

* * * * *